(12) United States Patent
Hong et al.

(10) Patent No.: US 9,175,415 B2
(45) Date of Patent: Nov. 3, 2015

(54) HYBRID NANOMATERIAL ELECTRODE AND FABRICATION METHOD THEREOF

(71) Applicant: NATIONAL TSING HUA UNIVERSITY, Hsinchu (TW)

(72) Inventors: Chien-Chong Hong, Hsinchu (TW); Zi-Xiang Lin, Hsinchu (TW); Kuo-Chu Hwang, Hsinchu (TW)

(73) Assignee: NATIONAL TSING HUA UNIVERSITY, Hsin-Chu (TW)

( * ) Notice: Subject to any disclaimer, the term of this patent is extended or adjusted under 35 U.S.C. 154(b) by 247 days.

(21) Appl. No.: 13/875,051

(22) Filed: May 1, 2013

(65) Prior Publication Data

US 2014/0174155 A1    Jun. 26, 2014

(30) Foreign Application Priority Data

Dec. 24, 2012    (TW) .............................. 101149566 A (51) Int. Cl.

| G01N 27/00 | (2006.01) |
|---|---|
| C25D 13/16 | (2006.01) |
| G01N 27/12 | (2006.01) |
| C25D 13/02 | (2006.01) |
| B82Y 15/00 | (2011.01) |

(52) U.S. Cl.
CPC ................ *C25D 13/16* (2013.01); *C25D 13/02* (2013.01); *G01N 27/128* (2013.01); *B82Y 15/00* (2013.01)

(58) Field of Classification Search
CPC ...... C25D 13/02; C25D 13/16; G01N 27/128; B82Y 15/00
See application file for complete search history.

(56) References Cited

PUBLICATIONS

Zi-Xiang Lin , "Precise Assembly of Nanowires Based on Dielectrophoresis and Its Applications in Violatile Organic Compounds Sensors", Hsinchu, Taiwan(R.O.C.).

*Primary Examiner* — Laura Martin
*Assistant Examiner* — Alex Devito
(74) *Attorney, Agent, or Firm* — WPAT, P.C.; Anthony King; Kay Yang (57) ABSTRACT

The present invention provides a hybrid nanomaterial electrode, comprising a pair of spaced-apart electrodes, at least three pairs of metallic nanowires disposed between the electrodes and respectively connected with the electrodes, and at least a detecting material connecting with the metallic nanowires. The detecting material is formed as a semiconductor nanostructure or a conductor nanostructure. The hybrid nanomaterial electrode of the present invention can be used in a gas detector for detecting volatile organic compounds, and has the advantage of providing high sensitivity, low detection limit, and the ability to operate at room temperature.

10 Claims, 12 Drawing Sheets

HYBRID NANOMATERIAL ELECTRODE AND FABRICATION METHOD THEREOF

CROSS-REFERENCES TO RELATED APPLICATIONS

This application claims priority to Taiwan Patent Application No. 101149566 filed on 24 Dec. 2012. All disclosure of which is incorporated herein by reference in its entirety.

BACKGROUND OF THE INVENTION

1. Field of the Invention

The present invention relates to hybrid nanomaterial electrodes, and more particularly to hybrid nanomaterial electrodes used in a gas detector for detecting volatile organic compounds.

2. The Prior Arts

Volatile solvents and oils are frequently used in industrial applications. The evaporation of the industrial solvent can form volatile organic compounds (VOCs) dangerous to the health that is propagated in the air. Common examples of volatile organic compounds include not completely burnt oxide carbon, hydrocarbons, alkene, benzene, alcohol, aldehyde, ketons, organic compounds including nitride, alkyl halides, etc.

Volatile organic compounds are dangerous to the health. Short and temporary exposure to volatile organic compounds can cause dizziness, nausea, eye tearing, nose irritation, coughing, and even death if the concentration is excessively high. Prolonged exposure can cause lever, lung and respiratory diseases or cancers. Moreover, because they usually include hydrocarbon elements, have a low evaporation point and are easily burnt, high concentrations of volatile organic compounds may induce explosion and incendiary risks. Therefore, the detection and control of the presence of volatile organic compounds is needed to reduce these risks.

A conventional gas analyzer instrument, such as a gas chromatography instrument or mass spectrometer, can have high sensitivity and provide accurate results and a low concentration detection limit. However, it is usually large in size and not conveniently portable, relatively expensive, and the need of sampling. Therefore, the conventional gas analyzer instruction is not adapted for frequently repeated and instantaneous uses.

One type of gas detectors may typically use semiconductor materials that can have variable resistance. The semiconductor detector has a high sensitivity, is simple in structure, small in size and cost-effective to fabricate. An example of material used the semiconductor detector is titanium dioxide. The gas detector using dioxide titanium as detecting material advantageously has a high sensitivity, is cost-effective to fabricate, fast response time, and short recovery time. However, this type of gas detector usually operates at a high temperature above 300° C., which limits its application. Moreover, the installation of the titanium dioxide nanostructure (nanowires, nanotubes, nanoposts or nanostrips) on the detecting electrode requires highly accurate processing, because the quality of the assembled titanium dioxide nanostructure determines the performance of the gas detector.

Dielectrophoresis is a process in which a non-uniform electric field is externally applied to control particles owing to interaction between the electric field and the dielectric property of the particles. This process can be applied for accurately assembling nanostructures, and can be implemented in room temperature to assemble a titanium dioxide nanostructure. Test experiments have shown that dielectrophoresis can be employed to accurately assemble a single nanowire on the electrode. However, if the titanium dioxide nanowire were to be assembled in a gap between two electrodes, the inventors of the present application have discovered that the nanowire can be installed with higher accuracy when the gap between the two electrodes is smaller. But the reduction of the inter-electrode gap renders the fabrication of the electrodes more difficult and requires an electron beam lithography and etching processes, which is complex, time consuming and costly.

SUMMARY OF THE INVENTION

To address the foregoing issues, the present invention provides a hybrid nanomaterial electrode comprising two electrodes spaced apart from each other by a gap, at least three pairs of metallic nanowires crossing the gap and respectively connected with the two electrodes, and at least a detecting material connecting with the metallic nanowires, the detecting material being formed as a semiconductor nanostructure or a conductive nanostructure.

According to one embodiment, the hybrid nanomaterial electrode includes a single beaded electrically conductive channel of a curved shape formed by an electrical sintering process associating a pulse electric field with an organic solvent.

The detecting material is formed as a nanowire or a nanofilm. The metallic nanowires are made of gold, silver, copper, aluminum, tungsten or brass. The semiconductor nanostructure includes titanium dioxide nanowires, or titanium dioxide nanowires including metallic particles.

The present invention also provides a method of fabricating a hybrid nanomaterial electrode, comprising:

a. forming at least three metallic nanowires between two electrodes by dielectrophoresis;

b. breaking the metallic nanowires to form a gap therein;

c. forming a detecting material in the gap by dielectrophoresis to connect the broken metallic nanowires, wherein the detecting material is formed as a semiconductor nanostructure or a conductive nanostructure; and d. forming a single electrically conductive channel in a polar organic solvent by applying an electrical sintering process associating a pulse electric field with the polar organic solvent, wherein the pulse electric field is applied as an external voltage instantly rise to 20 $V_{p-p}$.

According to one embodiment, step b. is performed in air or a solvent, and includes electrically sintering and burning the metallic nanowires to break the metallic nanowires and form the gap.

The detecting material used in the method is formed as a nanowire or a nanofilm. The metallic nanowires are made of gold, silver, copper, aluminum, tungsten or brass. The semiconductor nanostructure includes titanium dioxide nanowires, or titanium dioxide nanowires including metallic particles.

The hybrid nanomaterial electrode fabricated according to the present invention can be employed in a gas detector that is operable at room temperature, has high sensitivity, and can detect a low concentration of volatile organic compounds smaller than 10 ppm (and even as low as 1 ppm). The gas detector using the hybrid nanomaterial electrode does not need complex and expensive processing steps such as electron beam lithography and etching.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

The present invention provides a hybrid nanomaterial electrode and its fabrication process. A first embodiment of the fabrication method is described with reference to FIGS. 1-3. The electrode fabricated according to a particularly preferred embodiment is applied in a gas detection experiment described with reference to FIGS. 4-7 for determining its ability to detect certain gas compounds.

EXAMPLE 1

Preparation of a Hybrid Nanomaterial Electrode

In one embodiment, the present invention provides a method to fabricate hybrid nanowires. More specifically, electrically-sintered dielectrophoresis is applied to assemble nanostructures of metal and the detecting materials that are of different natures on a same pair of electrodes.

The metallic nanowire can be exemplary made of silver, and the detecting material can be made of titanium dioxide. A pair of flat electrodes spaced apart from each by a distance of about 60 μm can be used to assemble the nanowires in a micro flow channel having a height of about 60 μm. Ethanol can be used as solvent for the silver nanowire and the titanium dioxide nanowire. The nanowire and the solvent can be mixed at any ratios, for example 0.5-10 mg/mL. The assembly time may increase as the content of the nanowire lowers. The mixture of the silver nanowire and the titanium dioxide nanowire dissolved in the solvent can flow through the micro flow channel at a flow rate of about 5 μL/min The above pair of electrodes can be formed according to the following method. A glass wafer is prepared as a substrate for the electrodes. An electron gun then can be applied to plate a metallic bonding layer (for example, titanium) with a thickness of 25 nm and an electrode material with a thickness of 400 nm on the substrate (for example, gold). The glass wafer then can be placed in a spinning sputter machine to form a positive photoresist layer (S-1818). A first spin sputtering stage can be applied at a rotation speed of 500 rpm for 10 seconds to uniformly scatter the photoresist layer, and then a second spin sputtering stage can be applied at a rotation speed of 4000 rpm for 40 seconds to make the photoresist layer thinner. Once the deposition of the photoresist layer is completed, the substrate can be placed in a furnace to heat a temperature of 105° C. for 1 minute.

Once the pattern of the electrode is defined via a photo mask, the wafer is placed in an I-line UV exposing machine for exposure to UV radiation at an energy amount of 256 mJ/cm$^2$ for 13 seconds. The wafer then is immersed in a developer bath of tetramethylammonium hydroxide (TMAH, 2.38%) to remove the exposed portion of the photoresist layer, thereby only the pattern of the electrode remains. Cleaning with deionized water (DI) then is performed, followed with a drying step by applying a flow of nitrogen. Subsequently, an etching step is performed to selectively etch the different metallic layers, followed with deionized water cleaning and drying with a nitrogen flow. The photoresist layer acting as a protection layer then is removed with actone, followed with methanol and deionized water cleaning, and then drying with a nitrogen flow. The pair of electrodes can be thereby formed on the substrate.

Figure 1A:
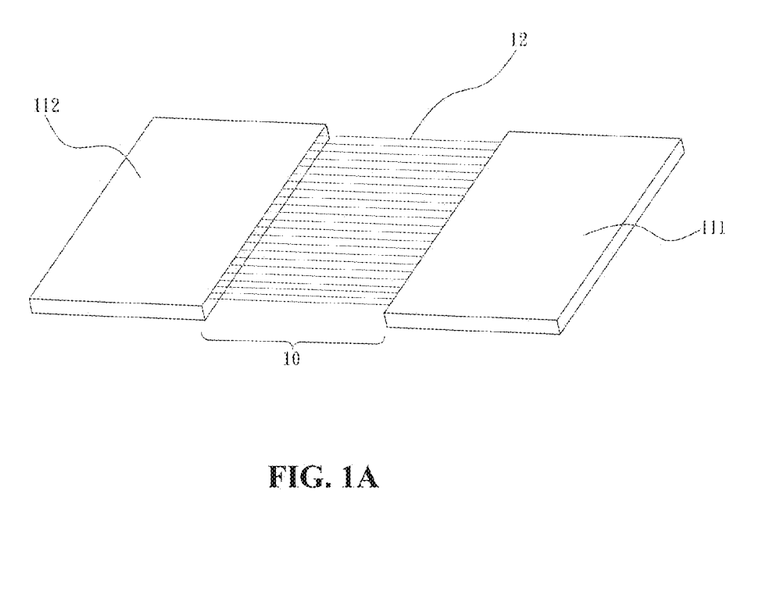
FIGS. 1A-1D are schematic views showing different states in the fabrication of a hybrid nanomaterial electrode according to one embodiment.
Figure 1B:
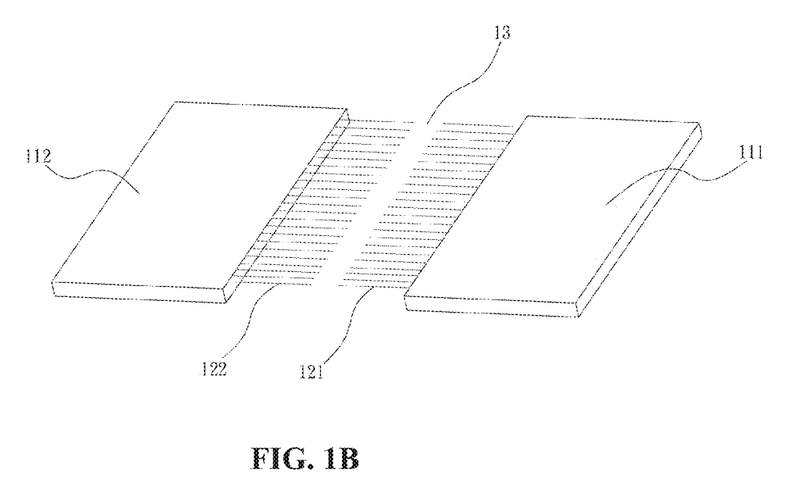

FIGS. 1A-1D show different states in the fabrication of the hybrid nanomaterial electrode. First, dielectrophoresis is applied to assemble three or more silver nanowires 12 in a gap 10 between two micro electrodes 111 and 112. The externally applied alternating voltage of the dielectrophoresis is 10 $V_{p-p}$, and the frequency is 10 kHz, as shown in FIG. 1A. Then the silver nanowires 12 are electrically sintered, and then burnt to break into three or more pairs of metallic nanowires 121 and 122, which thereby forms a gap 13 as shown in FIG. 1B. In this regard, the electrical sintering process can be processed in air or in a solution. Subsequently, an ethanol solution containing titanium dioxide nanowire is flowed through the micro flow channel at a flow rate of 5 μL/min.

Figure 1C:
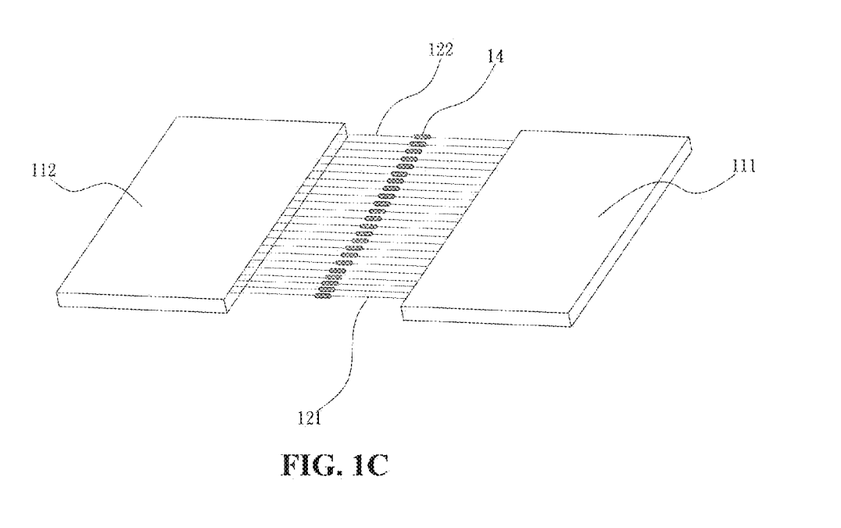

Similarly, dielectrophoresis is applied to assemble a detecting material, wherein the externally applied alternating voltage of the dielectrophoresis is also 10$V_{p-p}$, and the frequency is 10 kHz. The detecting material can have a semiconductor nanostructure or a conductor nanostructure including, without limitation, titanium dioxide nanowires, or titanium dioxide nanowires including metallic particles. In one embodiment, titanium dioxide nanowires 14 are used to connect the discontinued pairs of silver nanowires 121 and 122 as shown in FIG. 1C. Ultimately, a buffer solution is flowed to remove unconnected titanium dioxide nanowires 14, which prevents undesirable deposition arrangements. Aside silver nanowires, other materials can be used such as, without limitation, gold, copper, aluminum, tungsten or brass nanowires. Moreover, the structure of the detecting material can include nanowires or nanofilms.

Figure 2A:
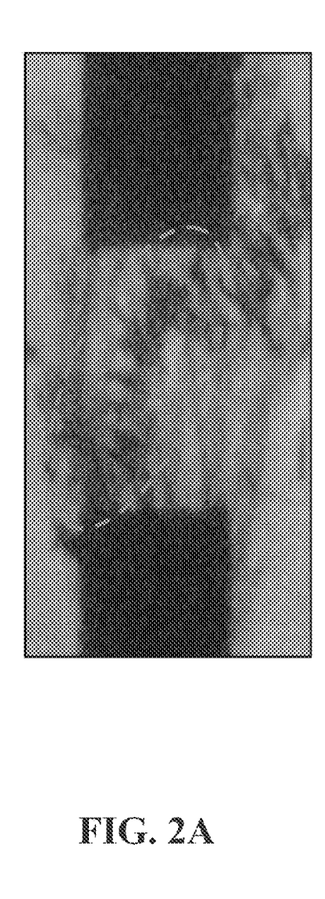
FIG. 2A is an image of the hybrid nanomaterial electrode observed through a microscope.
Figure 2B:
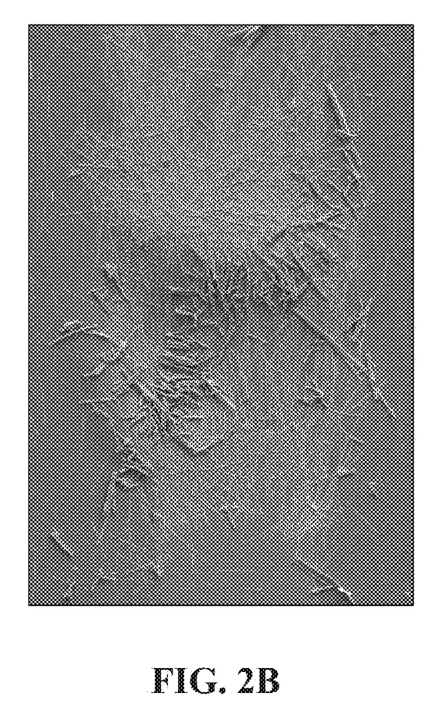
FIG. 2B is a SEM (scanning electron microscope) image of the hybrid nanomaterial electrode.

FIGS. 2A and 2B show the assembly structure. The region delimited with dotted lines indicates the titanium dioxide nanowires that connect with the silver nanowires. Regardless of whether the silver nanowires are broken in air or the ethanol solution, the formed electrodes have not significant differences in shape and impedance.

A scanning electron microscope can be used to observe the size of the gap after the silver nanowires are broken, which is between about 100 nm and 2 μm.

In the dielectrophoresis process described above, the titanium dioxide nanowires cannot be successfully assembled in the gap between the micro electrodes when the gap is relatively larger (for example when the gap is larger than the length of the titanium dioxide nanowires, such as greater than about 5-10 μm). Therefore, an embodiment of the present invention can first arrange the silver nanowires, reduce the gap of the micro electrodes to be equal to the length of the titanium dioxide nanowires, and then arrange the titanium dioxide nanowires between the silver nanowires. Because they have good conductivity, the silver nanowires can serve as part of the micro electrodes. By applying the hybrid dielectrophoresis process as described herein, silver nanowires can be used to connect micro electrodes that do not need to have a substantially small inter-electrode gap. As a result, the cost of the expensive and complex electron beam lithography process conventionally applied can be saved.

Figure 1D:
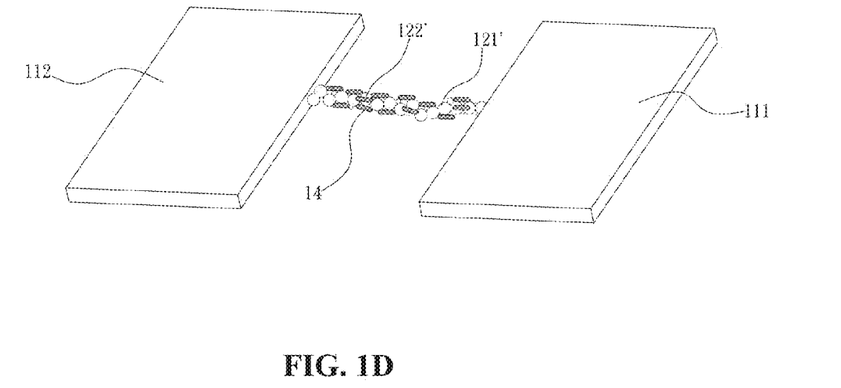
Figure 3A:
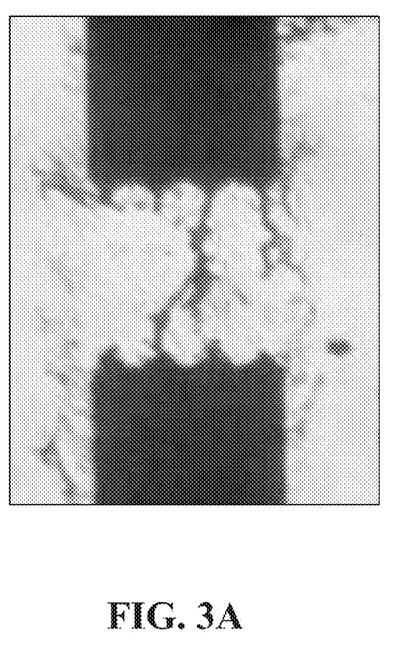
FIG. 3A is a microscope image of a hybrid nanomaterial electrode fabricated with an electrical sintering process applied on a nanostructure associating a pulse electric field with an organic solvent.
Figure 3B:
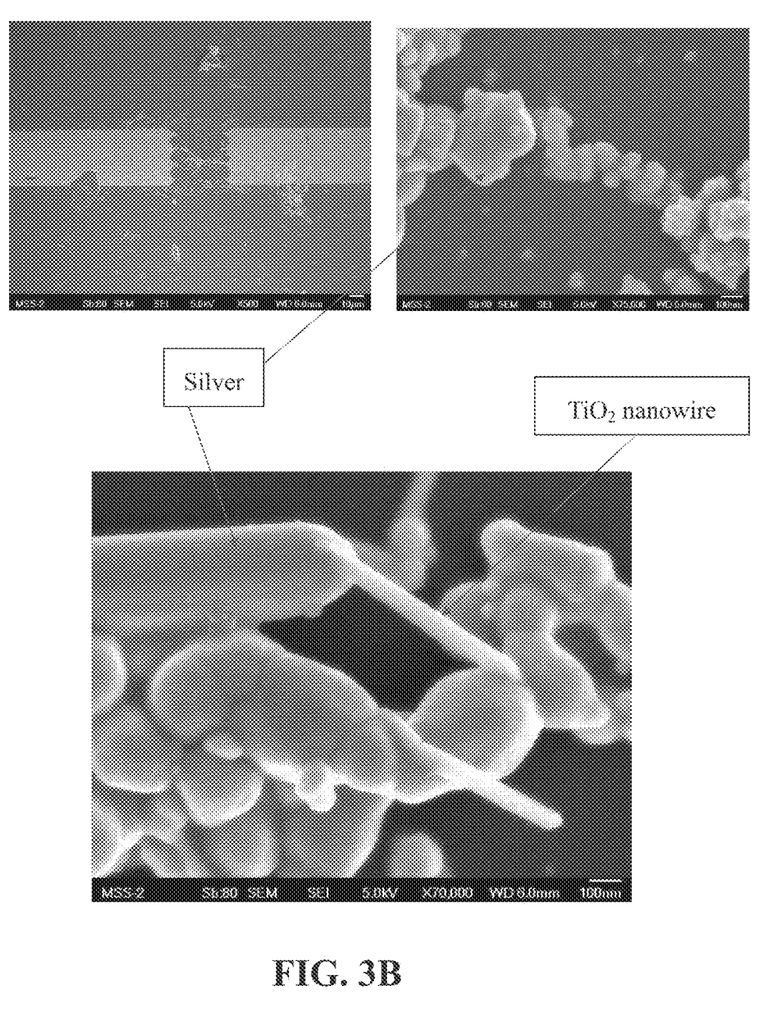
FIG. 3B is a SEM image of a hybrid nanomaterial electrode fabricated with an electrical sintering process applied on a nanostructure associating a pulse electric field with an organic solvent.

Referring to FIG. 1D, the electrode including the titanium dioxide nanowires then can undergo the electrical sintering process in which it is immersed in a solvent that is applied with a pulse electric field for forming a single electrically conductive channel. The solvent can be a polar solvent or an organic solvent. In one embodiment, the solvent can exemplary be ethanol. The electrical sintering process can abruptly raise the externally applied voltage to 20 $V_{p-p}$ (100 μA, 100 kHz, 130 ms), such that the titanium dioxide nanowires and the silver nanowires form a single electrically conductive channel of a elongated curved shape including adjacent beads, as schematically shown in FIGS. 3A and 3B. The formation of the structure as shown is due to partial melt of the silver nanowires when the applied voltage rises, which then form the beaded nanowires 121' and 122'. Owing to the presence of the titanium dioxide nanowires between the silver nanowires, the silver and titanium dioxide nanowires can form a conductive channel in the gap between the micro electrodes. With this method, nanowires can be disposed in an inter-electrode gap equal to 10, 20, 40, 60 μm or even greater, to form electrical connection.

EXAMPLE 2

Use of a Hybrid Nanomaterial Electrode in a Gas Detection Application

In one embodiment, the photocatalysis property of the titanium dioxide nanowire with respect to ultraviolet is used to detect volatile organic compounds. In particular, titanium dioxide has properties similar to semiconductor and can respectively produce pairs of free electrons and holes in the conduction band and the valence band after it has been excited by light. The pairs of electrons and holes are then transferred to react with the reactants adhered on the surface of the titanium dioxide in a reduction reaction.

In other words, the titanium dioxide nanowires when excited by light produce electron and hole carriers. These two types of carriers have a sufficient life cycle to propagate to the material surface and combine with the reactants adhered on its surface to produce a reduction reaction. In particular, the electrons can react with electron acceptors adhered on the surface of the titanium dioxide nanowires, which cause the transfer of electrons formed by excitement of the nanowires. As a result, a depletion region is formed in the surface of the nanowires, which causes a rise of the impedance value in the entire system. On the other hand, the holes can associate with electron donors on the surface of the titanium dioxide nanowires, which causes the impedance value of the nanowires to decrease. If no volatile organic compound reacts with the surface of the titanium dioxide nanowires, the electrons and holes produced by UV excitement can recombine together, which results in no change in the overall impedance.

A hybrid nanomaterial electrode using the above mechanism is applied in a gas detector chip. The gas detector chip is implemented to detect three different volatile organic compounds: ethanol, acetone and $NH_3$. Usually, either the impedance change is increased or the impedance of the dielectrophoresis electrode chip is reduced to increase the sensitivity in detecting the volatile organic compounds. One embodiment of the present invention reduces the impedance of the dielectrophoresis electrode chip by using a hybrid method. Accordingly, the sensitivity in detecting the volatile organic compounds can be substantially increased.

Figure 4:
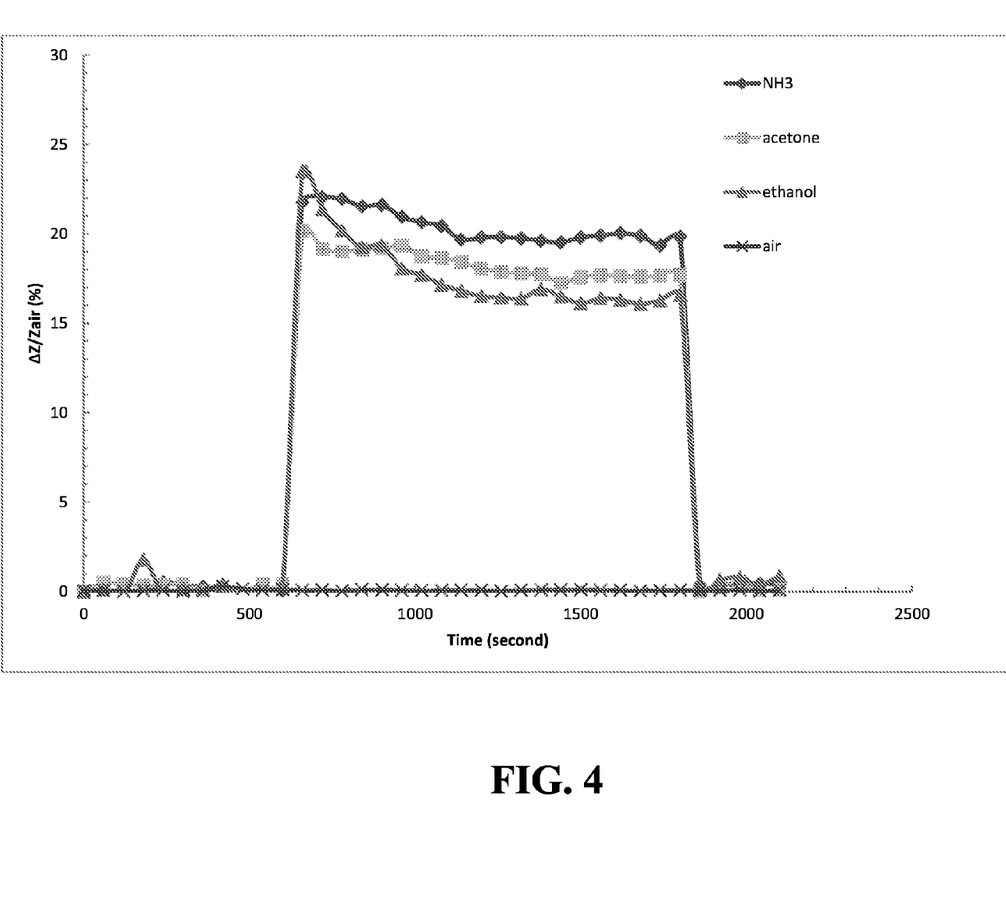
FIG. 4 shows the impedance change of a hybrid nanomaterial electrode chip of FIG. 1C in the presence of three volatile organic compounds.
Figure 5:
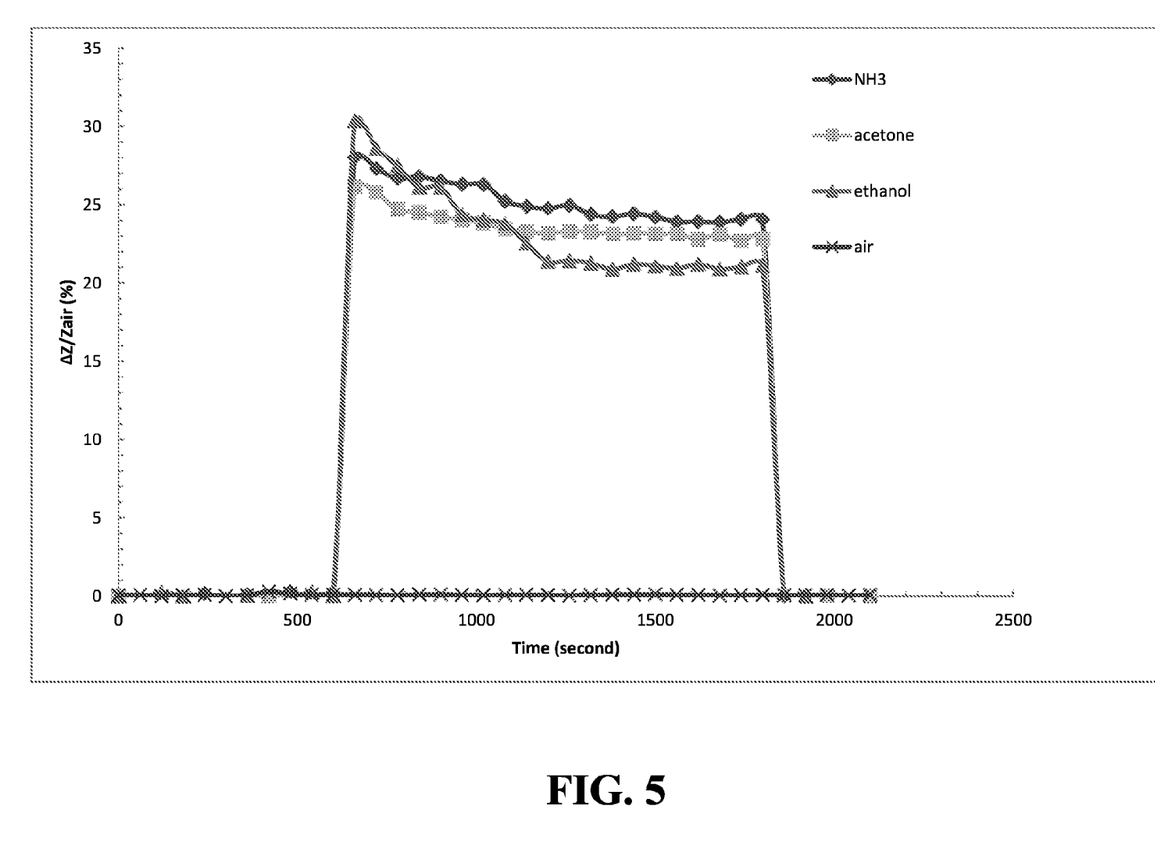
FIG. 5 shows the impedance change of a hybrid nanomaterial electrode chip of FIG. 1D in the presence of three volatile organic compounds, the hybrid nanomaterial electrode chip having undergone an electrical sintering process associating a pulse electric field with an organic solvent.

FIG. 4 shows the impedance change of a hybrid nanomaterial electrode chip of FIG. 1C in the presence of three volatile organic compounds. In the presence of ethanol, the greatest impedance change is 23.48%. In the presence of $NH_3$ and acetone, the impedance change is respectively 21.75% and 20.17%. Subsequently, air is flowed in so that the hybrid nanomaterial electrode chip can recover its initial impedance value. FIG. 5 shows the impedance change of a hybrid nanomaterial electrode chip of FIG. 1D in the presence of three volatile organic compounds, the hybrid nanomaterial electrode chip having undergone an electrical sintering process associating a pulse electric field with an organic solvent. In the presence of ethanol, the greatest impedance change is 30.34%. Air is then flowed in to have the nanomaterial electrode chip recover an initial impedance value. Moreover, when only air is flowed in, regardless of whether the nanomaterial electrode chip has undergone an electrical sintering process associating a pulse electric field with an organic solvent, the impedance of the nanomaterial electrode chip exhibits no change.

In one comparative example, a pair of flat-type electrodes with an inter-electrode gap of 20 μm and a pair of finger-type electrodes with an inter-electrode gap of 10 μm respectively undergo dielectrophoresis to form titanium dioxide nanowires. The conditions of the dielectrophoresis include an AC electric field equal to 10 $V_{p-p}$, and a flow rate of the titanium dioxide dissolved in ethanol equal to 10 μL/min The chip obtained from the above flat-type electrode arranged with the nanowires (also called "Electrode 1" hereafter) can have a greatest impedance change equal to 10.11% in the presence of ethanol, and an impedance change equal to 7.47% and 7.44% respectively in the presence of $NH_3$ and acetone. On the other hand, the chip obtained from the above finger-type electrode arranged with the nanowires (also called "Electrode 2" hereafter) can have a greatest impedance change equal to 14.33% in the presence of ethanol, and an impedance change equal to 13.53% and 12.52% respectively in the presence of $NH_3$ and acetone. Compared to Electrode 1, Electrode 2 exhibits an impedance change that is higher by about 4-6%. However, the impedance change is still lower than that of the hybrid nanomaterial electrode chip fabricated according to the present invention with or without an electrical sintering process associating a pulse electric field with an organic solvent. Therefore, even if the inter-electrode gap of the hybrid nanomaterial electrode fabricated according to the present invention is as high as 60 μm, which is higher than the inter-electrode gap of 10 μm or 20 μm of the electrodes described above, it can have a sensitivity higher than that of the electrodes with smaller inter-electrode gaps.

The testing results show that the hybrid nanomaterial electrode chip has a sensitivity in detecting volatile organic compounds that is substantially higher than that of Electrode 1 and Electrode 2. The reason is that the dielectrophoresis electrode chip assembled with the hybrid method has an impedance that is substantially smaller than that of Electrode 1 and Electrode 2. Since the sensitivity is calculated according to the expression ΔZ/Z, the reduction of the impedance can substantially increase the sensitivity in detecting volatile organic compounds.

Figure 6:
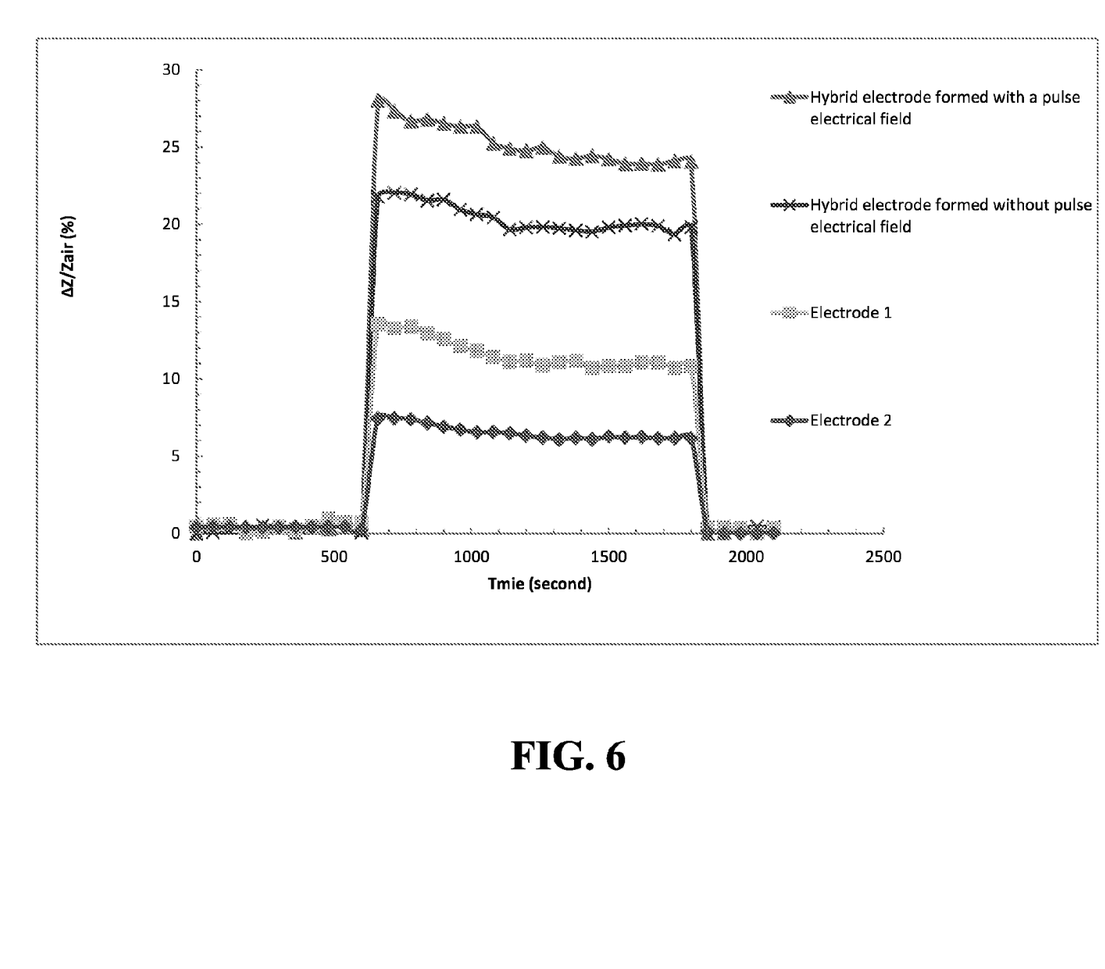
FIG. 6 shows the results of testing the impedance change of Electrode 1, Electrode 2, and the hybrid nanomaterial electrode fabricated with or without an electrical sintering process associating a pulse electric field with an organic solvent (i.e. hybrid electrode formed with or without a pulse electric field) in the presence of $NH_3$ at a concentration of 100 ppm.

FIG. 6 shows the results of testing the impedance change of Electrode 1, Electrode 2, and the hybrid nanomaterial electrode fabricated with or without an electrical sintering process associating a pulse electric field with an organic solvent in the presence of $NH_3$ at a concentration of 100 ppm. It can observed that the hybrid nanomaterial electrode fabricated with an electrical sintering process associating a pulse electric field with an organic solvent has the highest impedance change, and the hybrid nanomaterial electrode fabricated without the electrical sintering process has a relatively smaller impedance change. Moreover, the hybrid nanomaterial electrode fabricated according to the present invention either with or without the electrical sintering process has an impedance change that is substantially higher than that of the other electrodes. Therefore, the present invention can increase the sensitivity in detecting volatile organic compounds by reducing the impedance, and reduce the detection limit of the volatile organic compounds.

Figure 7:
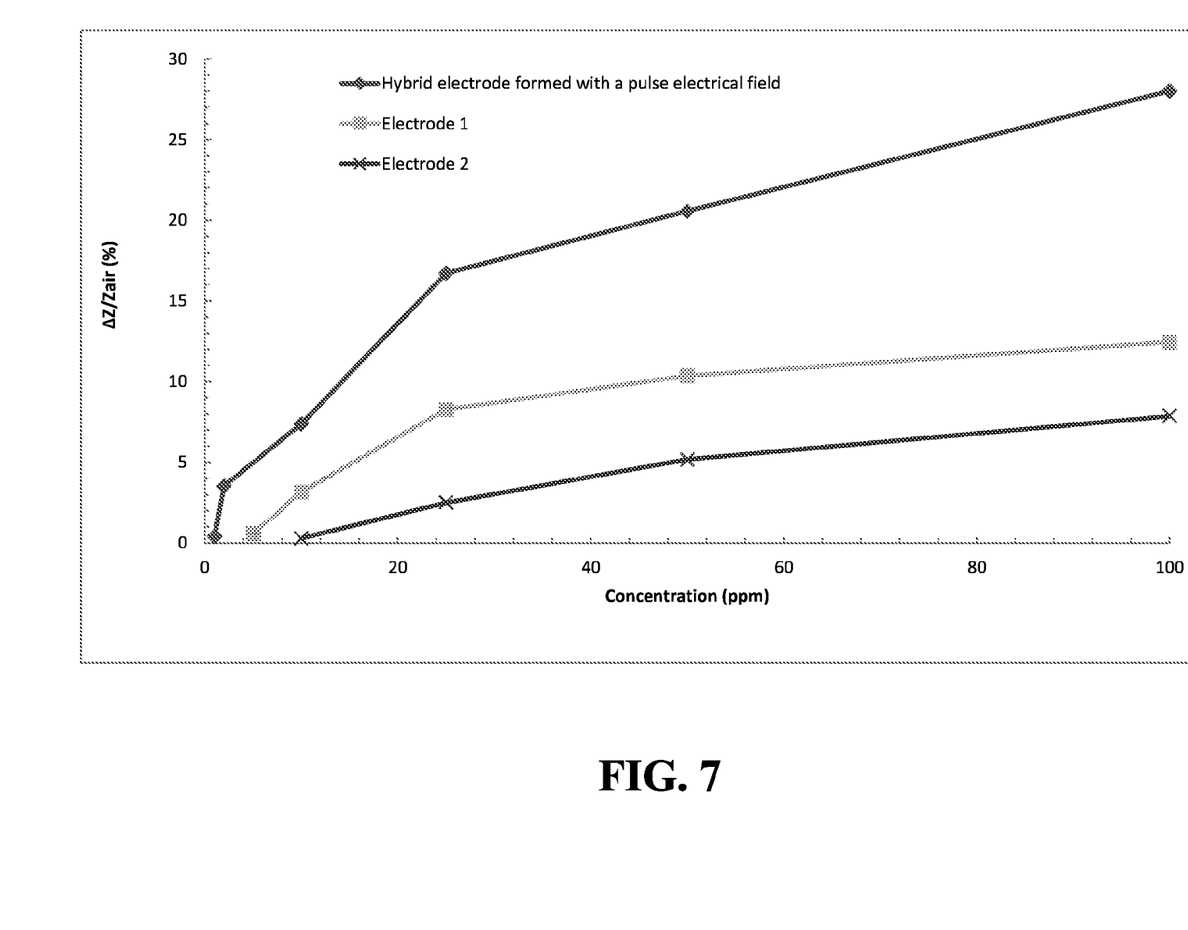
FIG. 7 shows a relation between the concentration of $NH_3$ and the impedance change of Electrode 1, Electrode 2 and the hybrid nanomaterial electrode fabricated according to the present invention either with or without the electrical sintering process associating a pulse electric field with an organic solvent (i.e. hybrid electrode formed with pulse electric field).

FIG. 7 shows a relation between the concentration of $NH_3$ and the impedance change of Electrode 1, Electrode 2 and the hybrid nanomaterial electrode fabricated according to the present invention either with or without the electrical sintering process. When the concentration of $NH_3$ is 100 ppm, the impedance change of Electrode 2 is 12.46%, and the impedance change of the hybrid nanomaterial electrode is 28.02%. In particular, the hybrid nanomaterial electrode in the presence of the concentration of $NH_3$ equal to 100 ppm has a sensitivity that is substantially increased and is at least 2-3 times higher that of Electrode 1 and Electrode 2. The reason is that it has an impedance substantially lower than that of the other dielectrophoresis chips. The detection limit of Electrode 2 is about 5 ppm, and its impedance change is 0.56%. In contrast, the hybrid nanomaterial electrode fabricated according to the present invention with the electrical sintering process has a detection limit equal to about 1 ppm, and an impedance change equal to 0.4%.

Moreover, suitable metal particles can be added in the titanium dioxide nanowires, which can promote the split of the electrons and holes and facilitate the photocatalysis reaction. The metal particles can include platinum (Pt), silver (Ag), gold (Au), ruthenium (Ru), and palladium (Pd).

As described above, the hybrid nanomaterial electrode fabricated according to the present invention does not require complex and expensive processing steps (such as photolithography and etching) to form a pair of electrodes with a substantially small inter-electrode gap. In the application of volatile organic compounds detection, it can provide a high impedance change, high sensitivity, and low detection limit (about 1 ppm). Moreover, the nanomaterial can be activated by ultraviolet to detect gas compounds at room temperature, and does not need to operate at a high temperature. In addition, the hybrid nanomaterial electrode fabricated with the electrical sintering process associating a pulse electric field with an organic solvent can have an impedance that is further reduced, which can further increase its sensitivity, thereby offering a wide range of applications.

The foregoing description is intended to only provide illustrative ways of implementing the present invention, and should not be construed as limitations to the scope of the present invention. While the foregoing is directed to embodiments of the present invention, other and further embodiments of the invention may thus be devised without departing from the basic scope thereof, and the scope thereof is determined by the claims that follow.

What is claimed is:

1. A hybrid nanomaterial electrode comprising:
   two electrodes spaced apart from each other by a gap; and
   a single electrically conductive channel with a shape of twisted bead strand crossing the gap and connected with the two electrodes;
   wherein the single electrically conductive channel is formed by at least three pairs of metallic nanowires and a detecting material coupled in the each pair of metallic nanowires via an electrical sintering process associating a pulse electric field with an organic solvent.

2. The hybrid nanomaterial electrode of claim 1, wherein the detecting material is formed as a nanowire or a nanofilm.

3. The hybrid nanomaterial electrode of claim 1, wherein the metallic nanowires are made of gold, silver, copper, aluminum, tungsten or brass.

4. The hybrid nanomaterial electrode of claim 1, wherein the detecting material is selected from the group consisting of titanium dioxide nanowires, and titanium dioxide nanowires including metallic particles.

5. The hybrid nanomaterial electrode of claim 1, wherein the gap is about 10-60 μm.

6. A gas detector excited by ultraviolet, including the hybrid nanomaterial electrode of claim 1.

7. The gas detector of claim 6, being operable at room temperature, and being capable of detecting a concentration of a volatile organic compound lower than 10 ppm.

8. A method of fabricating a hybrid nanomaterial electrode, comprising:
   a. forming at least three metallic nanowires between two electrodes by dielectrophoresis;
   b. breaking the metallic nanowires to form a gap therein;
   c. forming a detecting material in the gap by dielectrophoresis to connect the broken metallic nanowires, wherein the detecting material is formed as a semiconductor nanostructure or a conductive nanostructure; and
   d. forming a single electrically conductive channel in a polar organic solvent by applying an electrical sintering process associating a pulse electric field with the polar organic solvent, wherein the pulse electric field is applied as an external voltage abruptly rise to 20 $V_{p-p}$.

9. The method of claim 8, wherein the metallic nanowires are made of gold, silver, copper, aluminum, tungsten or brass.

10. The method of claim 8, wherein the detecting material is selected from the group consisting of titanium dioxide nanowires, and titanium dioxide nanowires including metallic particles.

* * * * *